(12) United States Patent  
Benecke et al.

(10) Patent No.: US 8,940,914 B2  
(45) Date of Patent: Jan. 27, 2015

(54) ESTERS OF 5-HYDROXYMETHYLFURFURAL AND METHODS FOR THEIR PREPARATION

(75) Inventors: Herman P. Benecke, Upper Arlington, OH (US); Jerry L. King, II, Crawfordsville, IN (US); Alex Walter Kawczak, Dublin, OH (US); Donald W. Zehnder, II, Hilliard, OH (US); Erica E. Hirschl, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 147 days.

(21) Appl. No.: 13/554,525

(22) Filed: Jul. 20, 2012

(65) Prior Publication Data

US 2013/0190516 A1 Jul. 25, 2013

Related U.S. Application Data

(62) Division of application No. 12/278,512, filed as application No. PCT/US2007/003399 on Feb. 7, 2007, now Pat. No. 8,247,582.

(60) Provisional application No. 60/771,169, filed on Feb. 7, 2006, provisional application No. 60/771,548, filed on Feb. 7, 2006.

(51) Int. Cl.
*C07D 307/54* (2006.01)
*C07D 307/46* (2006.01)

(52) U.S. Cl.
CPC .......... *C07D 307/54* (2013.01); *C07D 307/46* (2013.01)
USPC .......................................... 549/473; 549/488

(58) Field of Classification Search
CPC ........................... C07D 307/46; C07D 307/54
USPC .................................................. 549/473, 488
See application file for complete search history.

(56) References Cited

U.S. PATENT DOCUMENTS

| 2,813,113 | A | 11/1957 | Goebel |
| 3,024,260 | A | 3/1962 | Ernst |
| 3,437,437 | A | 4/1969 | Dorwart |
| 4,032,565 | A | 6/1977 | Kilpatrick et al. |
| 4,055,606 | A | 10/1977 | Prevorsek et al. |

(Continued)

FOREIGN PATENT DOCUMENTS

| DE | 1941522 | 4/1971 |
| DE | 1 745 448 | 9/1971 |

(Continued)

OTHER PUBLICATIONS

Chundry et al., "Preparation of polymeric Building Blocks from 5-Hydroxymethyl- and 5-Chloromethylfurfuraldehyde," Ind. Eng. Chem. Prod. Res. Dev., vol. 20, 1981, pp. 158-163.

(Continued)

*Primary Examiner* — Kristin Vajda
*Assistant Examiner* — Valerie Rodriguez-Garcia
(74) *Attorney, Agent, or Firm* — Greer Burns & Crain, Ltd.

(57) ABSTRACT

Disclosed are compositions and methods for the production of mono-esters and di-esters from the reaction of HMF and a reactant selected from a diacid or a diacid derivative; typical reactants are PAN, phthaloyl dichloride, dimethyl phthalate, maleic acid, and maleic anhydride or mono-esters that can be prepared from HMF and MAN.

21 Claims, 9 Drawing Sheets

Diols may include 1,6-Hexane Diol, Neopentyl Glycol, Cyclohexanedimethanol, other Alkyl Diols, Polyethylene Glycols, and Polypropylene Glycols

(56) References Cited

U.S. PATENT DOCUMENTS

| | | |
|---|---|---|
| 4,164,506 A | 8/1979 | Kawahara |
| 4,205,115 A | 5/1980 | Piccirilli et al. |
| 4,242,254 A | 12/1980 | Abolins |
| 4,242,309 A | 12/1980 | Carduck |
| 5,126,170 A | 6/1992 | Zwiener et al. |
| 5,324,794 A | 6/1994 | Taka et al. |
| 5,520,708 A | 5/1996 | Johnson |
| 5,534,425 A | 7/1996 | Fehr et al. |
| 5,638,637 A | 6/1997 | Wong et al. |
| 5,714,670 A | 2/1998 | Fehr et al. |
| 5,763,745 A | 6/1998 | Fehr et al. |
| 5,981,781 A | 11/1999 | Knowlton |
| 6,130,297 A | 10/2000 | Ramesh |
| 6,174,501 B1 | 1/2001 | Noureddini |
| 6,248,939 B1 | 6/2001 | Leto et al. |
| 6,420,490 B1 | 7/2002 | DuBois |
| 6,448,318 B1 | 9/2002 | Sandstrom |
| 6,479,445 B1 | 11/2002 | Machac, Jr. et al. |
| 6,483,008 B1 | 11/2002 | Dehesh et al. |
| 6,504,003 B1 | 1/2003 | Trout |
| 6,583,302 B1 | 6/2003 | Erhan |
| 6,699,945 B1 | 3/2004 | Chen et al. |
| 6,770,801 B2 | 8/2004 | Leto et al. |
| 6,833,341 B2 | 12/2004 | Machac, Jr. et al. |
| 6,956,155 B1 | 10/2005 | Martinez/Force et al. |
| 6,974,846 B2 | 12/2005 | Garrison et al. |
| 7,109,392 B1 | 9/2006 | Broglie et al. |
| 7,122,250 B2 | 10/2006 | Kinsho et al. |
| 7,205,457 B1 | 4/2007 | Kishore et al. |
| 7,244,857 B2 | 7/2007 | Fox et al. |
| 7,423,198 B2 | 9/2008 | Yao et al. |
| 7,531,718 B2 | 5/2009 | Fillatti |
| 7,566,813 B2 | 7/2009 | Voelker et al. |
| 7,589,222 B2 | 9/2009 | Narayan et al. |
| 7,601,677 B2 | 10/2009 | Graiver et al. |
| 7,601,888 B2 | 10/2009 | Fillatti et al. |
| 7,994,354 B2 | 8/2011 | Benecke et al. |
| 2001/0046549 A1 | 11/2001 | Sekula |
| 2002/0058774 A1 | 5/2002 | Kurth |
| 2002/0099229 A1 | 7/2002 | Martinez Force et al. |
| 2003/0024011 A1 | 1/2003 | Dehesh et al. |
| 2003/0119686 A1 | 6/2003 | Machac, Jr. et al. |
| 2003/0172399 A1 | 9/2003 | Fillatti |
| 2004/0006792 A1 | 1/2004 | Fillatti et al. |
| 2004/0088758 A1 | 5/2004 | Martinez Force et al. |
| 2004/0107460 A1 | 6/2004 | Fillatti et al. |
| 2004/0108219 A1 | 6/2004 | Matsumura |
| 2005/0010069 A1 | 1/2005 | Fitchett |
| 2005/0034190 A9 | 2/2005 | Fillatti et al. |
| 2005/0063939 A1 | 3/2005 | Ameer et al. |
| 2005/0072964 A1 | 4/2005 | Rapp |
| 2005/0145312 A1 | 7/2005 | Herberger, Sr. et al. |
| 2005/0150006 A1 | 7/2005 | Kodali et al. |
| 2005/0262589 A1 | 11/2005 | Fillatti |
| 2006/0080750 A1 | 4/2006 | Fillatti et al. |
| 2006/0199748 A1 | 9/2006 | Costello et al. |
| 2006/0206963 A1 | 9/2006 | Voelker et al. |
| 2007/0028328 A1 | 2/2007 | Brogie et al. |
| 2007/0175793 A1 | 8/2007 | Narine |
| 2007/0214516 A1 | 9/2007 | Fillatti et al. |
| 2007/0265459 A1 | 11/2007 | Suppes |
| 2007/0276165 A1 | 11/2007 | Gutsche |
| 2008/0021232 A1 | 1/2008 | Lin |
| 2008/0057552 A1 | 3/2008 | Lee |
| 2008/0081883 A1 | 4/2008 | King et al. |
| 2008/0091039 A1 | 4/2008 | Sleeter |
| 2008/0222756 A1 | 9/2008 | Fillatti et al. |
| 2008/0260933 A1 | 10/2008 | Thompson et al. |
| 2008/0262259 A1 | 10/2008 | Luo |
| 2008/0312082 A1 | 12/2008 | Kinney et al. |
| 2009/0082483 A1 | 3/2009 | Petrovic et al. |
| 2009/0119805 A1 | 5/2009 | Fillatti et al. |
| 2009/0202703 A1 | 8/2009 | Despeghel et al. |
| 2009/0216040 A1 | 8/2009 | Benecke et al. |
| 2009/0271893 A1 | 10/2009 | Fillatti |
| 2009/0276911 A1 | 11/2009 | Despeghel et al. |
| 2010/0029523 A1 | 2/2010 | Benecke et al. |
| 2011/0269978 A1 | 11/2011 | Garbark |
| 2011/0269979 A1 | 11/2011 | Benecke |
| 2011/0269981 A1 | 11/2011 | Benecke et al. |
| 2011/0269982 A1 | 11/2011 | Benecke |

FOREIGN PATENT DOCUMENTS

| | | |
|---|---|---|
| EP | 0 351 073 | 1/1990 |
| EP | 0 420 789 A1 | 4/1991 |
| EP | 0 571 187 | 11/1993 |
| EP | 1 978 013 | 10/2008 |
| WO | WO97/40698 | 11/1997 |
| WO | WO02/059106 * | 8/2002 |
| WO | WO 03/050081 | 6/2003 |
| WO | WO03/106599 | 12/2003 |
| WO | WO 2004/099227 | 11/2004 |
| WO | WO2006/020716 | 2/2006 |
| WO | WO 2006/093874 | 9/2006 |
| WO | WO 2006/093877 | 9/2006 |
| WO | WO2006/094138 | 9/2006 |
| WO | WO2006/116502 | 11/2006 |
| WO | WO 2007/027223 | 3/2007 |
| WO | WO2007/041785 | 4/2007 |
| WO | WO2008/124265 | 10/2008 |
| WO | WO 2008/130646 | 10/2008 |
| WO | WO2009058368 | 5/2009 |
| WO | WO2009/085033 | 7/2009 |
| WO | WO 2010/078491 | 7/2010 |
| WO | WO 2010/078493 | 7/2010 |
| WO | WO 2010/078498 | 7/2010 |
| WO | WO 2010/078505 | 7/2010 |
| WO | WO2010104609 | 9/2010 |
| WO | WO 2011/041476 | 4/2011 |

OTHER PUBLICATIONS

Kuo et al., "Four New Compounds from the Seeds of *Cassia fistula*," J. Nat. Prod., vol. 65, 2002, pp. 1165-1167.

R. G. Ackman et al., Ozonolysis of Unsaturated Fatty Acids, Can. J. Chem., vol. 39, (1961) pp. 1956/1963.

Petrovic, Zoran S., Polyurethanes from Vegetable Oils, Kansas Polymer Research Center, Pittsburg State University, Pittsburg, USA, Polymer Reviews, 48:109/155, 2008.

US Office Action dated Feb. 16, 2010 pertaining to U.S. Appl. No. 11/864,043.

International Search Report and Written Opinion dated Jun. 22, 2010 pertaining to international Application No. PCT/US2009/069921.

International Search Report and Written Opinion dated Jun. 10, 2010 pertaining to International Application No. PCT/US2009/069932.

Sparks, Jr. "Oxidation of Lipids in a Supercritical-Fluid Medium" Literature review, reaction of oleic acid with gas oxidants; references chaper III, Mississippi State University, Mississippi US, May 2008, pp. 33-40, 68.

International Search Report and Written Opinion of the International Searching Authority pertaining to international Application No. PCT/US2010/000775, dated Oct. 26, 2010.

EOP Second Examination Report relating to EPO Patent Application No. 06824715.4, dated Feb. 24, 2011.

Extended European Search Report relating to EPO Application No. 10184843.0, dated Mar. 2, 2011.

Office Action pertaining to U.S. Appl. No. 11/864,043 dated Aug. 25, 2010.

J.L. Sebedio et al., Comparison of the Reaction Products of Oleic Acid Ozonized in BCl3-, HCl- and BF3-MeOH Media, Chemistry and Physics of Lipids, vol. 35, Jan. 1984, pp. 21-28.

International Search Report and Written Opinion dated May 26, 2011 pertaining to International Application No. PCT/US2010/050803.

International Search Report and Written Opinion dated Oct. 5, 2010 pertaining to International Application No. PCT/US2009/069909.

International Search Report and Written Opinion dated May 20, 2010 pertaining to International Application No. PCT/US2009/069913.

(56) References Cited

OTHER PUBLICATIONS

Zoran S. Petrovic et al., "Structure and Properties of Polyurethanes Prepared From Triglyceride Polyols by Ozonolysis", Biomacromolecules 2005, 6, pp. 713-719.

International Search Report and Written Opinion dated Aug. 2, 2007 pertaining to International Application No. PCT/US2006/016022.
International Search Report and Written Opinion dated Feb. 13, 2007 pertaining to International Application No. PCT/US2005/028428.

* cited by examiner

US 8,940,914 B2

ESTERS OF 5-HYDROXYMETHYLFURFURAL AND METHODS FOR THEIR PREPARATION

This application is a divisional application of U.S. patent application Ser. No. 12/278,512, filed Jan. 13, 2009 now U.S. Pat. No. 8,247,582, which is a U.S. National Phase under 35 U.S.C. §371 of International Application No. PCT/US2007/003399, filed Feb. 7, 2007, which claims the benefits of U.S. Provisional Application No. 60/771,169, filed Feb. 7, 2006; and U.S. Provisional Application No. 60/771,548, filed Feb. 7, 2006.

The provisional applications are incorporated by reference as if completely rewritten herein.

FIELD OF THE INVENTION

The present invention discloses new ester products of 5-hydroxymethylfurfural (HMF) with maleic acid and phthalic acid and its isomers. Esters of HMF with maleic anhydride (MAN), maleic acid, fumaric acid, and dialkylfumarate (e.g. dimethylfumarate) as well as the esters of phthalic anhydride (PAN), phthalic acid, phthalic esters as well as the analogous derivatives of isophthalic and terephthalic acid are disclosed. Mono-ester products are useful as a reactive diluent for adhesive, composite, coating, and ink applications. All esters disclosed herein can be used as heat activated crosslinkers for adhesives, coatings, composites, foundry binders, foams, or inks. The unsaturated esters can also be homopolymerized or copolymerized with other unsaturated monomers.

BACKGROUND OF THE INVENTION

A reported synthesis of di-ester involves the $S_N2$ displacement of 5-(chloromethyl)-2-furfuraldehyde with phthalic acid dipotassium salt. See Chundury, D.; Szmant, H. H. Ind. Eng. Chem. Prod. Res. Dev. 1981, 20, pp. 158-163. This method has moderate yields (65%) and results in the production of tar-like impurities which can only be efficiently removed by column chromatography. Reproduction of these reported experimental procedures under optimal conditions generated the desired compound in low yield with extensive impurities. These impurities appear to extend from the decomposition of 5-(chloromethyl)-2-furfuraldehyde. See Sanda, K.; Rigal, L.; Delmas, M.; Gaset, A. Synthesis 1992, 6, pp. 541-542.

The present invention provides new methods for production.

BRIEF DESCRIPTION OF THE INVENTION

A broad embodiment of the invention provides for new mono-esters and di-esters and methods for preparing the mono-ester and di-ester of 5-hydroxymethylfurfural with typically a diacid or the diacid derivative. Typical specific examples of useful diacids or diacid derivatives include: maleic anhydride, maleic acid, maleic acid di-esters, fumaric acid, fumaric ester, dimethylfumarate; and phthalic anhydride, phthalic acid, phthalic acid di-ester, phthaloyl dichloride, isophthalic acid, isophthalic di-esters, terephthalic acid, terephthalic di-ester, and the like. Typically the diacid or diacid derivative has various R and R' groups as further illustrated in the detailed description.

A further aspect of the invention includes a method for producing an ester of 5-hydroxymethylfurfural by the steps of mixing 5-hydroxymethylfurfural (HMF) and maleic anhydride or maleic acid for example; and reacting at a temperature between about 75° C. and about 150° C. to obtain the ester product. The reaction may be in the presence or absence of a catalyst. Typical products are mono-esters, di-esters, and mixtures thereof. In some embodiments temperatures of about 77° C. and about 120° C. are preferred.

A yet further aspect of the invention includes a method for producing an ester of 5-hydroxymethylfurfural by the steps of mixing 5-hydroxymethylfurfural (HMF) and phthalic anhydride (PAN); and reacting at a temperature between about 75° C. and about 150° C. to obtain the ester product. The reaction may be in the presence or absence of a catalyst. Typical products are mono-esters, di-esters, and mixtures thereof. In some embodiments temperatures of about 77° C. and about 120° C. are preferred.

Another aspect of the invention includes a method for producing a di-ester by the steps of reacting a mono-ester of HMF and PAN with a coupling agent (EDC) and HMF and an optional catalyst while maintaining the temperature between about −20° C. and about 50° C.

An additional aspect of the invention includes a method for producing a di-ester by the steps of reacting HMF and dimethyl phthalate at an elevated temperature in the presence of a catalyst. Typically the reaction temperature is above about 60° C. or more preferably above about 90° C.

A further aspect of the invention includes method for producing a di-ester by the steps of mixing HMF and a catalyst in a solvent; adding phthaloyl dichloride and reacting while maintaining the temperature between about −20° C. and about 50° C.

DETAILED DESCRIPTION OF THE INVENTION AND BEST MODE

Figure 1:
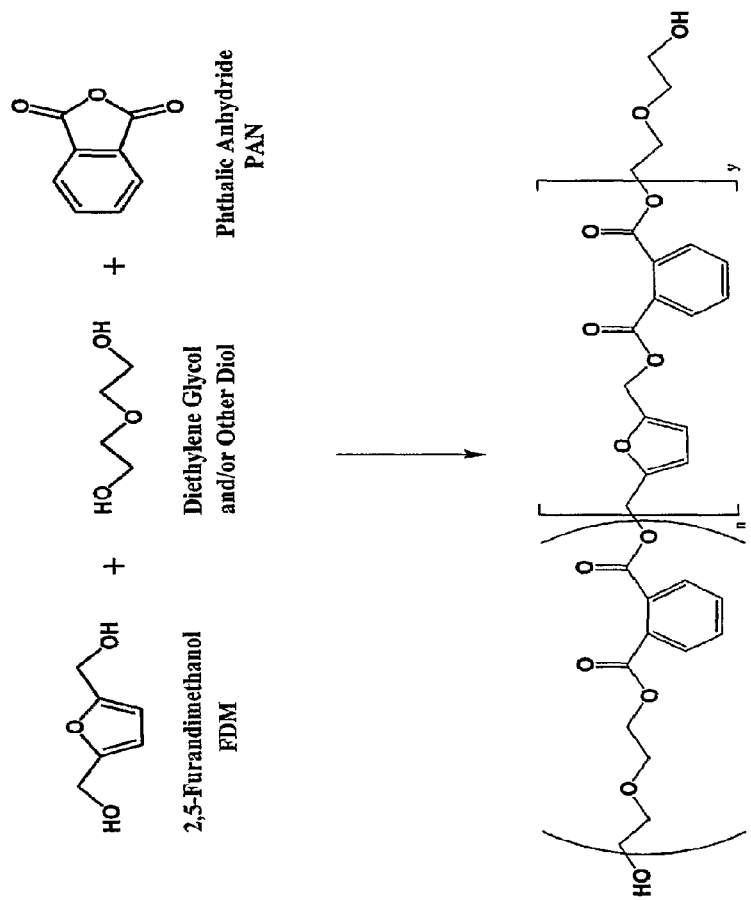
FIG. 1 illustrates the reaction of FDM with diethylene glycol and/or another diol and PAN.

A broad embodiment of the invention provides for new mono-esters and di-esters and methods for preparing the mono-ester and di-ester of 5-hydroxymethylfurfural with a diacid or the diacid derivative. Typical specific examples of useful diacids or diacid derivatives include:

Type I. reactants typified by the maleic acid group such as maleic anhydride, maleic acid, maleic acid di-esters, fumaric acid, fumaric ester, dimethylfumarate, and the like; and Type II reactants typified by phthalic anhydride, phthalic acid, phthalic acid di-ester, phthalic diacid chloride, isophthalic acid, isophthalic di-esters, isophthalic diacid chloride, terephthalic acid, terephthalic di-ester, terephthalic acid chloride, and the like. Typically the diacid or diacid derivative has various R and R' groups as further illustrated in the detailed description.

Reactants are typically selected from one or more of the reactants in Type I or II.

One aspect of the invention includes a new composition of matter disclosed below in Composition 1A as mono-ester 1, a maleic acid HMF mono-ester. The maleic acid HMF mono-ester may include additional R and R' groups as shown below.

Reaction 1

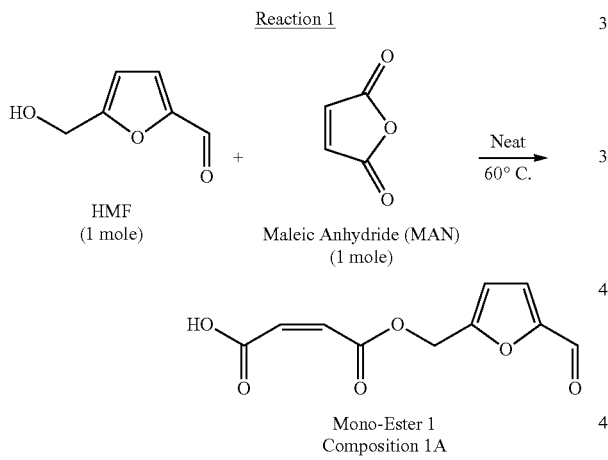

Composition 1B below illustrates the general product for the reaction for producing a mono-ester having various R and R' substituents.

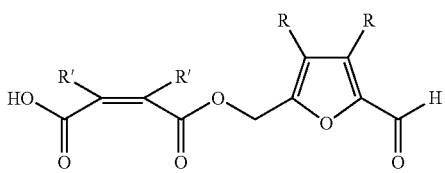

Maleic Acid HMF Mono-ester wherein R is the same or different, and each R is independently selected from the group consisting of H, alkyl having from 1 to 12 carbon atoms, and aryl having from about 6 to about −12 carbon atoms, or an arylalkyl having between about 7 to about 18 carbon atoms, additionally two adjoining R groups can be part of a fused aryl group such as a benzo group; and wherein R' is the same or different, and each R' is independently selected from the group consisting of H, alkyl having from 1 to 12 carbon atoms, and aryl having from 6-12 carbon atoms, or an arylalkyl having between about 7 to about 18 carbon atoms additionally two adjoining R' groups can be part of a fused aryl group such as a benzo group.

Typically in Reaction 1 maleic anhydride can be replaced with dialkyl fumarate to obtain the di-ester in Composition 1C. Generally, the unsaturated acid can be derived from either maleic acid or fumaric acid. The R and R' groups are the same as immediately above.

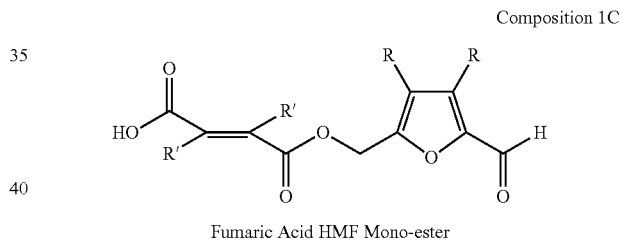

Fumaric Acid HMF Mono-ester

The mono-ester is typically prepared by adding the HMF to a reaction vessel, in contact with maleic anhydride, maleic acid, fumaric acid, dimethylfumarate or mixtures thereof and reacted. Typical temperatures for the reaction include temperatures at which the reactants melt up to about 120° C. Preferably the temperature is about the temperature at which the reactants melt to about 80° C. A lower temperature will result in increased production of the mono-ester versus the production of both mono-ester and di-ester, or predominantly di-ester, or increasing di-ester (Composition 2A) production as the temperature rises, see Reaction 2 below.

Reaction 2

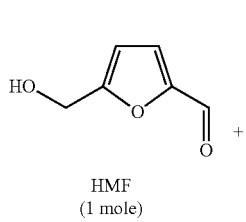

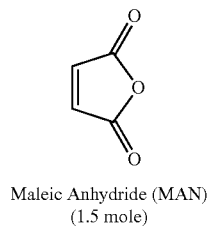

Maleic Anhydride (MAN)
(1.5 mole)

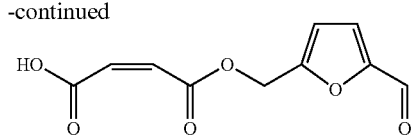

Neat
100° C.

-continued

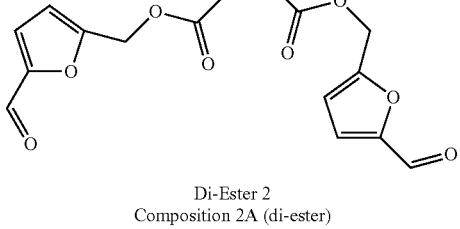

Mono-Ester 1

+

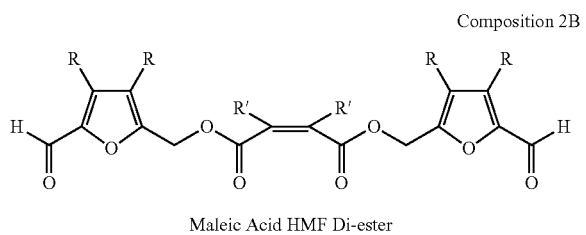

Di-Ester 2
Composition 2A (di-ester)

Composition 2B below illustrates the general product for the reaction for producing a di-ester having various R and R' substituents as outlined above.

Composition 2B

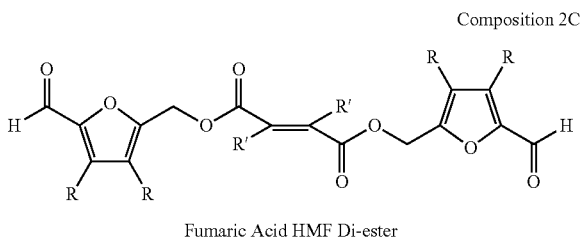

Maleic Acid HMF Di-ester

Typically in Reaction 2 maleic anhydride can be replaced with dialkyl fumarate to obtain the mono-ester of Composition 1C and the di-ester in Composition 2C. Generally, the unsaturated acid can be derived from either maleic acid or fumaric acid. The R and R' groups are the same as immediately above.

Composition 2C

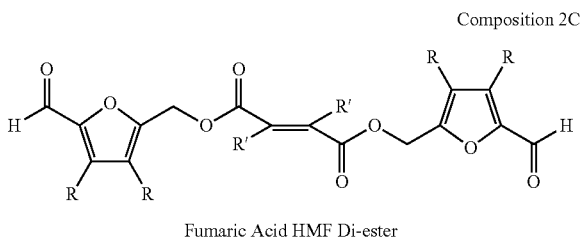

Fumaric Acid HMF Di-ester

Another embodiment of the invention includes a composition of matter as illustrated by the di-ester 2 in Composition 2A. The di-ester may include additional R and R' groups as shown, wherein R is the same or different, and each R is independently selected from the group consisting of H, alkyl having from 1 to 12 carbon atoms, and aryl having from about 6 to about –12 carbon atoms, or an arylalkyl having between about 7 to about 18 carbon atoms, additionally two adjoining R groups can be part of a fused aryl group such as a benzo group; and wherein R' is the same or different, and each R' is independently selected from the group consisting of H, alkyl having from 1 to 12 carbon atoms, and aryl having from 6-12 carbon atoms, or an arylalkyl having between about 7 to about 18 carbon atoms additionally two adjoining R' groups can be part of a fused aryl group such as a benzo group.

Typical temperatures for the reaction include temperatures from about 60° C. and higher with about 80° C. to about 120° C. being preferred. Preferably the temperature is at the higher end of the temperature range since di-ester is maximized at the higher temperatures.

Molar ratios of HMF:maleic anhydride (e.g. HMF:MAN) or HMF:ester (e.g. fumaric acid ester) typically range from about 4:1 to about 1:2. A ratio of about 4:1 to 2:1 favors the di-ester while a ratio from 1:1 to about 1:2 favors the mono-ester.

The reactions for making the above mono-esters and di-esters are typically made in the presence of non-reactive gas or inert gas (e.g. argon) to exclude air and atmospheric moisture so as to reduce unwanted side reactions. The mono-ester and/or di-ester product may be separated and purified using techniques known in the art. The reactions are typically performed without a catalyst and/or water scavenger; however, a catalyst and/or water scavenger may be used. If desired, a non-reactive solvent may be used in the reaction such as acetone, 2-butanone, tetrahydrofuran, and their mixtures thereof. Typically, solvent extraction and/or precipitation techniques are useful for purification based on the property that the mono-ester is water soluble and the di-ester is not. Possible purification systems include diethyl ether/water or chloroform/water. The product is typically filtered and washed.

Typical catalysts useful with the invention include: pyridine and (dimethylamino)pyridine; organic titanates; dibutyltin dilaurate; dibutyltin oxide; tin(II) chloride; magnesium ethoxide; carbodiimides; molecular sieves; basic or acidic ion exchange resins; toluene-sulfonic acid, sulfuric acid, and HCl; aluminum chloride, boron trifluoride, and boron trifluoride diethyletherate; clay; lanthanide complexes; and cation radicals.

In preparing the materials according to the invention it is noted that the order of addition and phase of the materials at time of addition can influence the relative amounts of mono-ester or di-ester that are produced.

One method includes the steps of adding and mixing solid reactants and then raising the temperature to produce a melt and subsequent reaction.

Another method includes the steps of melting the reactants to be reacted and adding them together in the molten state as a melt to a melt as they begin to react.

A yet further method includes the steps of melting one reactant and then adding another solid reactant to it.

Factors preferring the production of mono-ester include:
(1) use of mole ratios of HMF:(diacid or diacid derivative) of about 1:1 to about 1:2,
(2) order of addition wherein addition of HMF to the diacid or diacid derivative (in this case diacid or diacid derivative (e.g. MAN) will initially be in great excess) so that mono-ester is favored; conversely, adding MAN to HMF favors di-ester formation; and
(3) everything else being the same, a higher temperature of reaction favors di-ester while a lower temperature of reaction favors the mono-ester.

Example Set I

The following examples are intended to be illustrative of the invention and are not intended to limit the scope of the invention in any way.

Example I-1

This example illustrates the synthesis of mono-ester and di-ester from HMF and MAN (50585-16-28). The molar ratio of HMF:MAN is about 2:3.

HMF (30.25 g, 239.9 mmol) was charged to a 250 mL round bottom flask in a glove bag under argon. Maleic anhydride (MAN) (35.28 g, 359.8 mmol) was charged to the reactor with a continuous argon flow into the reactor. The reactor was blanketed with argon. The reaction mixture was heated to 100° C. with stirring under argon. The mixture was stirred for 20 hours at 100° C. During this reaction period, the mixture became a viscous blackish brown liquid. The crude product mixture was a very viscous liquid at room temperature. $^1$H NMR analysis showed that mono-ester and di-ester were present in the mixture.

Example I-2

This example illustrates the synthesis of mono-ester and di-ester from HMF and MAN. The molar ratio of HMF:MAN is about 1:1.

HMF (28.53 g, 226.2 mmol) was charged to a 250 mL round bottom flask in a glove bag under argon. Maleic anhydride (MAN) (33.28 g, 339.4 mmol) was charged to the reactor with a continuous argon flow into the reactor. The reactor was blanketed with argon. The reaction mixture was heated to 100° C. with stirring under argon. The mixture was stirred for 20 hours at 100° C. During this reaction period, the mixture became a viscous blackish brown liquid. The crude product mixture was a very viscous liquid at room temperature. $^1$H NMR analysis showed that mono-ester and di-ester were present in the mixture.

Example I-3

This example illustrates the synthesis of mono-ester from HMF and MAN. The molar ratio of HMF:MAN is about 1:1.

HMF (21.15 g, 167.7 mmol) was charged to a 250 mL round bottom flask in a glove bag under argon. Maleic anhydride (MAN) (16.49 g, 168.2 mmol) was charged to the reactor with a continuous argon flow into the reactor. The reactor was blanketed with argon. The reaction mixture was heated to 60° C. with stirring under argon. During the heating ramp, an exotherm was observed where the reaction mixture temperature rose to 76° C. The reaction mixture was allowed to cool to 60° C., where the molten liquid was stirred until it solidified (3.6 hours). $^1$H NMR analysis showed that this light brown solid product was 90% mono-ester.

Example I-4

This example illustrates the synthesis of mono-ester and di-ester products from HMF and dimethylfumarate.

The products are prepared using the procedure and conditions as in Examples I-1 to I-3 at temperatures of about 60° C. to about 120° C. Low temperatures result in a product that is substantially or mainly mono-ester. Higher temperatures as well as increasing amounts of HMF result in a mixture of increasing di-ester content.

Broadly, another aspect of the invention provides for a new composition of matter and a method for its synthesis. The composition is the esterification product of 5-hydroxymethylfurfural (HMF) and phthalic anhydride (PAN) (see Reaction 3 below).

The mono-ester derivative is typically prepared by:
(1) the reaction of HMF and PAN (or phthalic acid) without catalyst and/or water scavenger; or
(2) the reaction of HMF and PAN (or phthalic acid) with various catalysts including: pyridine and (dimethylamino) pyridine; organic titanates; dibutyltin dilaurate; dibutyltin oxide; tin(II) chloride; magnesium ethoxide; carbodiimides; molecular sieves; basic or acidic ion exchange resins; toluene-sulfonic acid, sulfuric acid, and HCl; aluminum chloride, boron trifluoride, and boron trifluoride diethyletherate; clay; lanthanide complexes; and cation radicals. Additionally, the reaction could be conducted with or without solvent.

Another aspect of the invention provides for the synthesis and isolation of the new mono-ester from 5-hydroxymethylfufural (HMF) and phthalic anhydride (PAN). High isolated yields, up to 91%, with good purity 94-98% were obtained by mixing the molten reactants at 95° C. No catalyst or solvent was needed for these preparations. The reactions take place quickly, transitioning from the molten phase to a solid phase after approximately 15 minutes of stirring. The mono-ester can easily be removed from the reactor by dissolving it in acetone or other solvent or solvent combinations. See reaction 3 and composition 3A below.

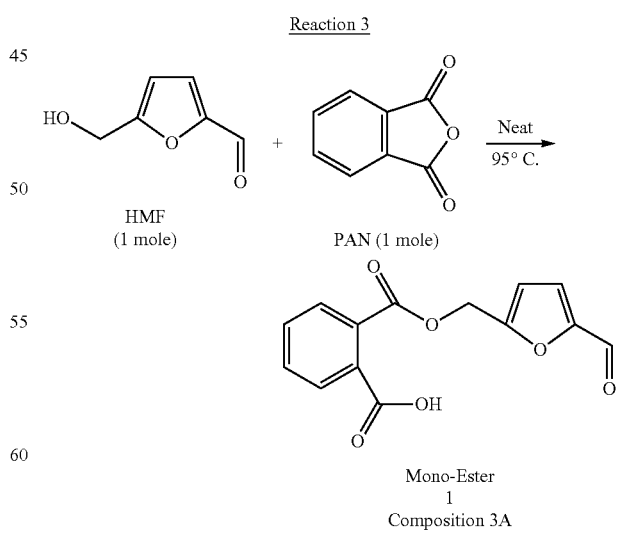

Reaction 3

HMF (1 mole) + PAN (1 mole) →(Neat, 95° C.)

Mono-Ester 1
Composition 3A

Composition 3B below illustrates the general product for the reaction for producing a di-ester having various R and R' substituents as outlined herein.

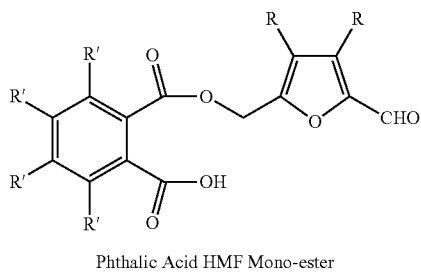

Phthalic Acid HMF Mono-ester wherein R is the same or different, and each R is independently selected from the group consisting of H, alkyl having from 1 to 12 carbon atoms, and aryl having from about 6 to about −12 carbon atoms, or an arylalkyl having between about 7 to about 18 carbon atoms, additionally two adjoining R groups can be part of a fused aryl group such as a benzo group; and
wherein R' is the same or different, and each R' is independently selected from the group consisting of H, alkyl having from 1 to 12 carbon atoms, and aryl having from 6-12 carbon atoms, or an arylalkyl having between about 7 to about 18 carbon atoms additionally two adjoining R' groups can be part of a fused aryl group such as a benzo group.

Temperatures of at least those required for melting and reacting may be used. Optional solvents used include THF and acetone.

The HMF/PAN esters described herein can be used in specific applications and/or they can be converted to selected new derivatives/polymer systems for use in adhesives, coatings, inks, plastics, or polymer additives. For example the mono-ester can be used as a reactive diluent for adhesives, coatings, and inks. The mono-ester and/or di-ester can be used as heat activated crosslinkers for adhesives, coatings and inks.

Another broad aspect of the invention provides for a new process for the synthesis of a di-ester from the 5-hydroxymethylfurfural (HMF) and phthalic anhydride (see Reaction 4 immediately below)

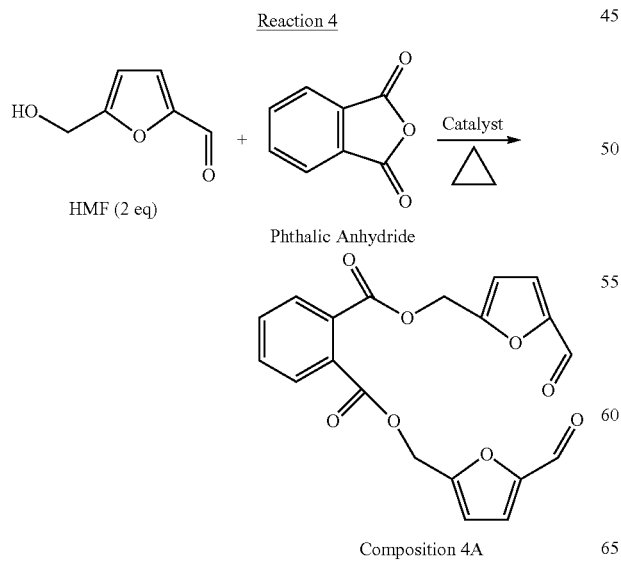

Composition 4B below illustrates the general product for the reaction for producing a di-ester having various R and R' substituents wherein R is the same or different, and each R is independently selected from the group consisting of H, alkyl having from 1 to 12 carbon atoms, and aryl having from about 6 to about −12 carbon atoms, or an arylalkyl having between about 7 to about 18 carbon atoms, additionally two adjoining R groups can be part of a fused aryl group such as a benzo group; and
wherein R' is the same or different, and each R' is independently selected from the group consisting of H, alkyl having from 1 to 12 carbon atoms, and aryl having from 6-12 carbon atoms, or an arylalkyl having between about 7 to about 18 carbon atoms additionally two adjoining R' groups can be part of a fused aryl group such as a benzo group. When R=H and R'=H composition 4A is obtained.

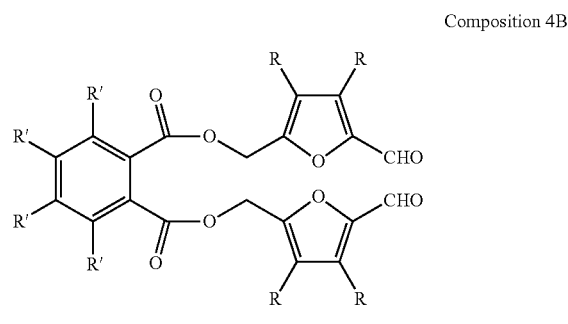

Phthalic Acid HMF Di-ester

In Reaction 4, phthalic anhydride can be substituted with isophthalic acid or terephthalic acid to obtain Compositions 4C or Composition 4D respectively.

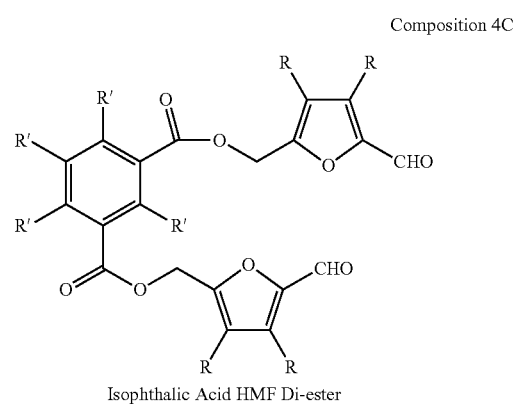

Isophthalic Acid HMF Di-ester

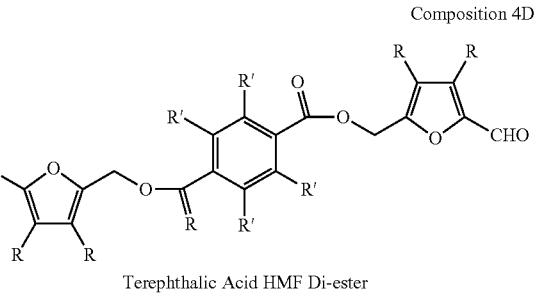

Terephthalic Acid HMF Di-ester

Referring again to Reaction 4, in another aspect of the invention in order to avoid steric hinderance the direct reaction of an acid in typical esterification chemistries could be used. Typically isomers of phthalic acid can be used including isophthalic acid and terephthalic acid.

Another aspect of the invention includes a method for di-ester synthesis from 5-(hydroxymethyl)-2-furfuraldehyde (HMF) and phthaloyl dichloride. HMF is mixed with an HCl scavenger (e.g. triethylamine, TEA) and a solvent the mixture is cooled to about −10° C. to about 10° C., phthalolyl dichloride is added and the mixture is reacted with mixing for 1-3 hours. The reaction may be quenched with water if desired and extracted by techniques known in the art. See Reaction 5 in Example 7 below.

Another aspect of the invention includes a method for di-ester synthesis from a mono-ester intermediate and HMF. The mono-ester of phthalic anhydride is mixed with a solvent and cooled to about −10° C. to about 10° C., a carbodiimide (e.g. EDC) is added and stirred for about 10 to 30 minutes. HMF is added along with an optional catalyst and reacted for at the cooled temperature for about 2 to about 20 hours. The reaction may be quenched with water if desired and extracted by techniques known in the art. Another useful coupling agent includes dicyclohexylcarbodiimide that can be used in esterification reactions. See Reaction 6 in Examples 8 and 9 below.

Another aspect of the invention includes a method for di-ester synthesis from 5-(hydroxymethyl)-2-furfuraldehyde (HMF) and dimethyl phthalate. HMF and dimethyl phthalate are mixed with a suitable catalyst and heated at about 80° C. to about 110° C. while stirring for about 2 to about 4 hours. See Reaction 7 in Example 10 below.

Another aspect of the invention includes a method for di-ester synthesis from 5-(hydroxymethyl)-2-furfuraldehyde (HMF) and phthalic anhydride. HMF is added to reaction vessel and melted, then PAN is added to the molten HMF while stirring. An optional esterification catalyst such as Tyzor TPT® may be used. The mixture is reacted while stirring for about 16 to about 30 hours at a temperature of about 110° C. to about 140° C. See Reaction 8 of Example 11 below.

Another aspect of the invention includes a method for di-ester synthesis by treating a mono-ester that is typically the reaction product of HMF and PAN with a molar equivalent of a coupling reagent such as carbonyldiimidazole (CDI) and adding HMF, the mixture was cooled to about −10° C. to about 10° C. and reacted for about 10 to 18 hours at the reduced temperature. See Example 12 below.

Example Set II

The following examples are illustrative of various aspects of the invention and are not meant to limit the scope of the invention in any way.

Example II-1

This example illustrates mono-ester synthesis from HMF and PAN) using PAN in excess.

HMF (32.40 g, 256.9 mmol) was charged to a 250 mL round bottom flask in a glove bag under argon. Phthalic anhydride (47.58 g, 321.2 mmol) was charged to the reactor with a continuous argon flow into the reactor. The reactor was blanketed with argon. The reaction mixture was heated to 100° C. with stirring under argon. The mixture was stirred for 18 hours at 100° C. During this reaction period, the mixture became blackish brown in color and very viscous. The crude produce mixture was a tacky semisolid at room temperature. $^1$H NMR analysis showed that mono-ester conversion was 85%.

Example II-2

This example is a repeat of Example II-1 and illustrates mono-ester synthesis from HMF and PAN using PAN in excess.

HMF (23.10 g, 183.2 mmol) was charged to a 250 mL round bottom flask in a glove bag under argon. Phthalic anhydride (PAN) (33.93 g, 229.1 mmol) was charged to the reactor with a continuous argon flow into the reactor. The reactor was blanketed with argon. The reaction mixture was heated to 100° C. with stirring under argon. The mixture was stirred for 18 hours at 100° C. During this reaction period, the mixture became blackish brown in color and very viscous. The crude produce mixture was a tacky semisolid at room temperature. $^1$H NMR analysis showed that mono-ester conversion was 83%.

Example II-3

This example illustrates mono-ester synthesis from HMF and PAN (equimolar amounts).

HMF (10.21 g, 80.96 mmol) was charged to a 250 mL round bottom flask in a glove bag under argon. The reactor was blanketed with argon. PAN (11.99 g, 80.96 mmol) was charged to a separate bottle under argon. The reactor was submerged into a preheated oil bath at 95° C. The HMF was allowed to totally melt. Then, the pre-weighed phthalic anhydride was added to the molten HMF with vigorous stirring. The mixture was stirred until the molten liquid solidified (about 15 minutes). The crude product was removed, pulverized to a fine powder with a mortar and pestle, and placed in a flask with a 30% solution of ethanol in water (100 mL). The mixture was stirred vigorously for 10 minutes, and filtered. The solid product was then washed with 100 mL aliquots of the 30% ethanol/water solution until HMF was not observed by thin layer chromatography (TLC). The product was dried under full vacuum at room temperature for 15 hours to afford mono-ester (16.60 g, 75%) as a light yellow solid. Mono-ester was 98% pure by $^1$H NMR. $^1$H NMR (500 MHz, $d_6$-DMSO): δ 9.61 (s, 1H), 7.81-7.78 (m, 1H), 7.66-7.64 (m, 3H), 7.55 (d, 1H, J=3.5 Hz), 6.88 (d, 1H, J=3.6 Hz)), 5.37 (s, 2H). $^{13}$C NMR ($d_6$-DMSO): δ 178.5, 167.7, 167.1, 154.9, 152.5, 131.8, 131.7, 131.5, 131.5, 129.0, 128.3, 123.7, 113.2, 58.8.

A light tan/white mono-ester (97+%) was prepared in 88% yield by adding a molar equivalent of phthalic anhydride to molten 5-hydroxymethylfufural (HMF) at 77° C. without catalyst. This mono-ester had a melting point of 130° C. and a decomposition temperature of 167° C. (rapid weight loss onset).

Two series of three reproducibility experiments were conducted at 77° C., one set with tetra-isopropyl titanate (Tyzor® TPT from DuPont, USA) catalyst and the other set without catalyst. The average mono-ester yield for the catalyzed reactions determined by NMR was 81.8±9.6%. The average mono-ester yield for the un-catalyzed reactions was 60.6±15.2%. The catalyzed reactions yielded a crude product that was darker in color (brown) than the un-catalyzed product (light tan). It was difficult to control these reactions because, after approximately 5-10 minutes of vigorous stirring, the molten reaction mixture quickly formed the hard solid mono-ester product.

Two mono-esterifications were then conducted at 90° C., one with Tyzor® TPT and one without catalyst. In this case, the un-catalyzed reaction yielded slightly more mono-ester (86% vs. 82%). In addition, 75% mono-ester was obtained from a preparation using acetone as the solvent.

Additional mono-esterification melt preparations were conducted on a small scale (about 5 g HMF) at temperatures ranging from 90° C. to 120° C. although in general temperature of 90° C. to 120° C. are expected to provide good results. (See Table I). No catalyst was used in this example. Since the highest yield was obtained at 95° C., this temperature was used for six repeat reactions. The six new reactions were at double the scale as before so as to lessen the yield percentage lost to transfer during isolation. The mole % mono-ester and corresponding isolated yield is listed for each reaction in Table II. The average isolated yield was 82±5% with mono-ester purity ranging from 94%-98%. The yields are expected to be higher at larger scales. Mono-ester preparation Sample 45-10 (see Table II) gave the highest yield (91.0%) because the crude product was not removed from the flask, pulverized, and filtered, like the other reaction preparations, thereby eliminating transfer losses. Thus, product purity was lower than most of the other products. In addition, mono-esters Sample 45-10 and Sample 44-7 were prepared from a different HMF batch than mono-ester Samples 44-10, 44-15, 44-24, and 44-27. Mono-ester Sample 44-15 was ground to a finer particle size to increase purity. As a result, its isolated yield was the lowest (74.8%). Mono-ester Samples 44, 44-24, and 44-27 had higher yields than mono-ester Sample 44-15 because less emphasis was placed on product purity. A light yellow solid mono-ester, same color as HMF, was produced in 15 minutes without catalyst and solvent.

TABLE I

Mono-Ester Yield at Different Reaction Temperatures

| Sample No. | Reaction Temperature (° C.) | Isolated Yield (%) |
|---|---|---|
| 27-33 | 90 | 65 |
| 33-5 | 95 | 76 |
| 35-4 | 100 | 70 |
| 36 | 105 | 68 |
| 38 | 110 | 71 |
| 41-8 | 115 | 23 |
| 43-7 | 120 | 27 |

TABLE II

HMF/PAN Mono-Ester Reproducibility Experiments at 95° C.

| Sample No. | Isolated Yield (%) | Mole % Mono-Ester (%) |
|---|---|---|
| 45-10 | 91.0 | 94.2 |
| 44-7 | 85.7 | 96.8 |
| 44-10 | 83.4 | 95.5 |
| 44-15 | 74.8 | 97.7 |
| 44-24 | 76.7 | 94.6 |
| 44-27 | 81.2 | 94.2 |
| Average | 82.1 ± 5.4 | 95.5 ± 1.3 |

Example II-4

This example illustrates the synthesis of mono-ester using tetra-isopropyl titanate as a catalyst.

HMF (5.66 g, 44.9 mmol) was charged to a 250 mL round bottom flask in a glove bag under argon. The reactor was blanketed with argon. PAN (6.65 g, 44.9 mmol) was charged to a separate bottle under argon. The reactor was submerged into a preheated oil bath (85° C.). The HMF was allowed to totally melt. Then, the pre-weighed phthalic anhydride was added to the molten HMF with vigorous stirring. The mixture was stirred for 5 minutes, then Tyzor TPT® (tetra-isopropyl titanate) (12.8 µL, 0.0432 mmol) was added to the mixture. The mixture stirred until the molten liquid solidified (7 minutes). Mono-ester yield was 82% as determined by $^1$H NMR.

Example II-5

This example illustrates the synthesis of mono-ester using pyridine as a catalyst with excess PAN.

HMF (14.54 g, 115.3 mmol) was charged to a 250 mL round bottom flask in a glove bag under argon. PAN (21.35 g, 144.1 mmol) was charged to the reactor with a continued argon flow into the reactor. The reactor was blanketed with argon. Anhydrous pyridine (32.3 µL, 0.399 mmol) was added to the reaction mixture by syringe. The reaction mixture was heated to 80° C. with stirring under argon. The mixture stirred until the molten liquid solidified (15 minutes). $^1$H NMR analysis showed mono-ester conversion was 96%. This example using excess PAN and pyridine catalyst gave the highest conversion.

Example II-6

This example illustrates the synthesis of mono-ester 1 using acetone as a solvent without catalyst.

HMF (6.67 g, 52.9 mmol) was charged to a 250 mL round bottom flask in a glove bag under argon. PAN (7.83 g, 52.9 mmol) was charged to the reactor with a continued argon flow into the reactor. The reactor was blanketed with argon. Acetone (45 mL) was added to the reaction mixture. The mixture was stirred under argon until most of the reactants had dissolved. The mixture became homogeneous when heated to a gentle reflux. The mixture was stirred at reflux under argon for 3 hours. A distillation take off adapter and receiver flask were then attached to the reactor. Acetone was distilled into the receiver flask as the mixture was heated to 90° C. The mixture was held at 90° C. for 30 minutes. Mono-ester yield was 76% as determined by $^1$H NMR.

Example II-7

This example illustrates di-ester synthesis from 5-(hydroxymethyl)-2-furfuraldehyde (HMF) and phthaloyl dichloride.

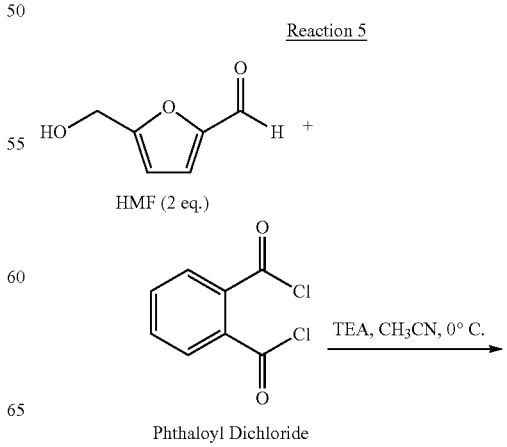

-continued

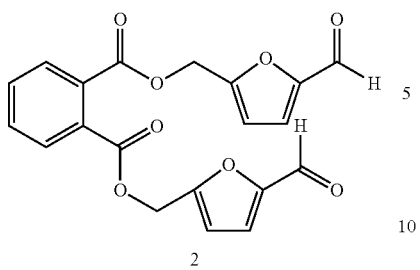

2

A dry 250 mL round bottom flask purged with nitrogen was charged with HMF (10 g, 79.3 mmol) and triethylamine (TEA)* (10.03 g, 13.93 mL, 99.12 mmol) in acetonitrile (200 mL) and then cooled to 0° C. Phthaloyl dichloride (8.04 g, 5.72 mL, 39.65 mmol) was added via syringe over 2 hours with rapid stirring and continued cooling. Once the addition was complete the reaction was stirred for 8 hours and allowed to warm to room temperature. The reaction was quenched with water (50 mL) and then transferred to a separatory funnel (1 L). Diethyl ether (300 mL) and 5% HCl (200 mL) were added to the funnel and then shaken for 2 minutes. After the solution separated, the aqueous layer was removed and the organic layer was re-extracted with 2 more 5% HCl aliquots (200 mL). After removing the aqueous layer, 10% sodium bicarbonate (200 mL) was added to the organic layer material and then shaken vigorously. After separation and removal of the aqueous layer, the remaining solution was washed with distilled water (100 mL). The organic layer was dried with magnesium sulfate, filtered and then concentrated to afford di-ester (14.4 g, 95%) as a pale yellow oil. $^1$H NMR ($d_6$-DMSO) δ 9.61 (s, 2H), 7.79-7.76 (m, 2H), 7.74-7.70 (m, 2H), 7.37 (d, J=3.5 Hz, 2H), 6.88 (d, J=3.5 Hz, 2H), 5.38 (s, 4H). $^{13}$C NMR ($d_6$-DMSO) δ 178.1, 165.0, 153.5, 151.5, 130.9, 129.6, 128.0, 122.6, 112.3, 57.8.

Most any amine base will work.

Example II-8

This example illustrates di-ester synthesis from mono-ester Intermediate and HMF.

Reaction 6

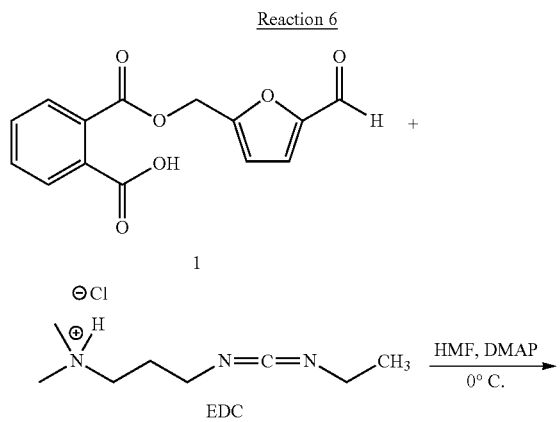

-continued

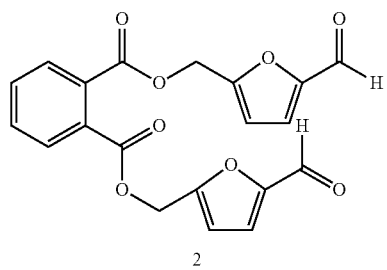

2

A dry 100 mL round bottom flask purged with nitrogen was charged with mono-ester (6 g, 21.8 mmol) in either anhydrous chloroform or anhydrous acetonitrile (50 mL) and then cooled to 0° C. The solution was treated with N-(3-Dimethylaminopropyl)-N'-ethylcarbodiimide hydrochloride (EDC) (4.24 g, 22.1 mmol) and then allowed to stir for 20 min. 5-(Hydroxymethyl)-2-furfuraldehyde (HMF) (2.74 g, 21.8 mmol) along with 4-dimethylamino pyridine (DMAP catalyst) (270 mg, 2.18 mmol) were added to the solution and then stirred for 10 hours while warming to room temperature. The reaction mixture was quenched with distilled water (40 mL) and then transferred to a separatory funnel (1 L) containing either chloroform or diethyl ether (300 mL) and 1% HCl (300 mL). The solution was extracted and then the aqueous layer was discarded. This process was repeated two more times. A 1% sodium bicarbonate solution (300 mL) was added and shaken for 2 min. After separation, the aqueous layer was removed followed by a final distilled water wash (100 mL) of the ether layer. The organic layer was dried with magnesium sulfate, filtered and then concentrated to afford di-ester (5.81 g, 70%) as a pale yellow oil. $^1$H NMR ($d_6$-DMSO) δ 9.61 (s, 2H), 7.79-7.76 (m, 2H), 7.74-7.70 (m, 2H), 7.37 (d, J=3.5 Hz, 2H), 6.88 (d, J=3.5 Hz, 2H), 5.38 (s, 4H). $^{13}$C NMR ($d_6$-DMSO) δ 178.1, 165.0, 153.5, 151.5, 130.9, 129.6, 128.0, 122.6, 112.3, 57.8.

Another carbodiimide that could be used is dicyclohexylcarbodiimide (DCC).

Example II-9

This example illustrates di-ester synthesis from mono-ester intermediate[1] and HMF.

Reaction 6

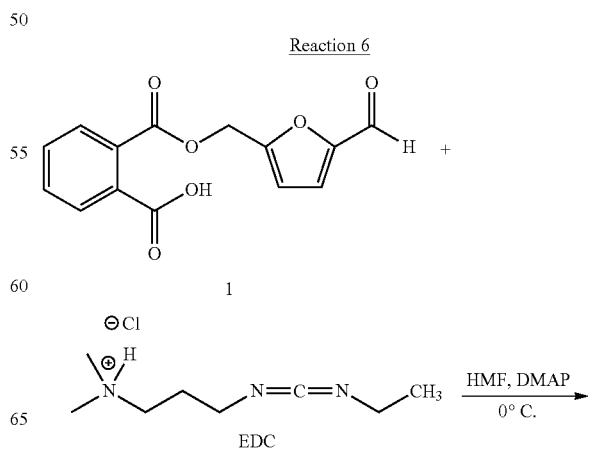

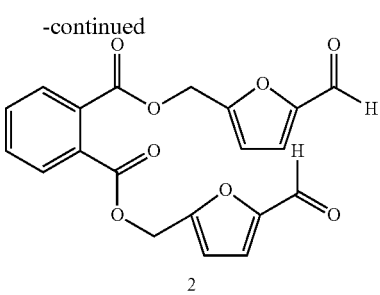

2

A dry 50 mL round bottom flask purged with nitrogen was charged with mono-ester (300 mg, 1.09 mmol) in anhydrous chloroform (20 mL) and then cooled to 0° C. The solution was treated with N-(3-Dimethylaminopropyl)-N'-ethylcarbodiimide hydrochloride (EDC) (209 mg, 1.09 mmol) followed by 5-(Hydroxymethyl)-2-furfuraldehyde (HMF) (137 mg, 1.09 mmol) then 4-dimethylamino pyridine (DMAP) (67 mg, 0.55 mmol). The solution was stirred for 15 hours while warming to room temperature. The reaction mixture was quenched with distilled water and then transferred to a separatory funnel (1 L) containing chloroform (20 mL). The aqueous layer was separated from the organic layer and treated with another 20 mL of chloroform. This process was repeated once more. The combined organic layers were dried with magnesium sulfate. The crude product was filtered, concentrated and purified by column chromatography on silica using 90:10 CHCl₃/ethyl acetate to afford di-ester (330 mg, 80%) as a pale yellow oil.

Example II-10

This example illustrates di-ester synthesis from 5-(hydroxymethyl)-2-furfuraldehyde (HMF) and dimethyl phthalate.

Reaction 7

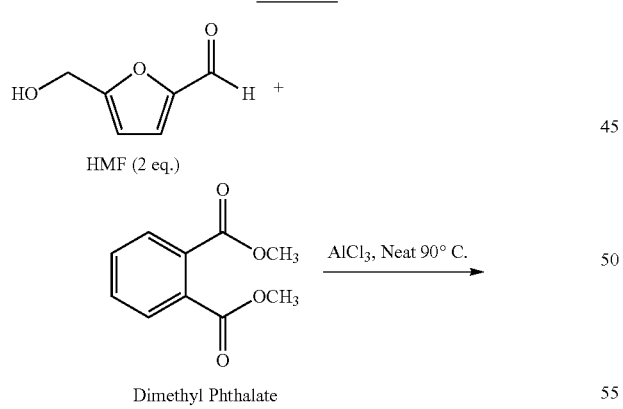

2

A dry 250 ml round bottom flask was charged with HMF (10 g, 79.3 mmol) and dimethyl phthalate (7.69 g, 39.65 mmol) and then heated to 90° C. with rapid stirring. After 2 hours, aluminum trichloride (AlCl₃) (1 mol %) was added and continued to heat and stir for 2 hours. The reaction produced di-ester in approximate 25% yield as a dark brown oil.

It was noted that no di-ester was observed at 90° C. until catalyst was added. Thus a higher reaction temperature appears to be needed without the presence of a catalyst.

Example II-11

This example illustrates the synthesis of a di-ester from 5-(hydroxymethyl)-2-furfuraldehyde and phthalic anhydride.

Reaction 8

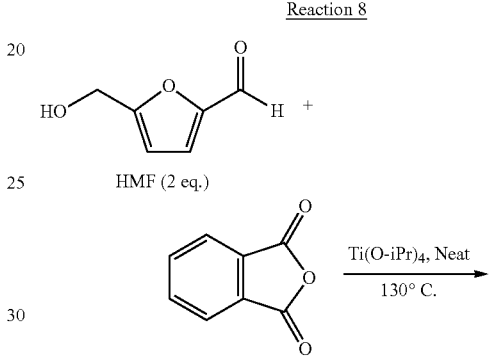

Phthalaic Anhydride

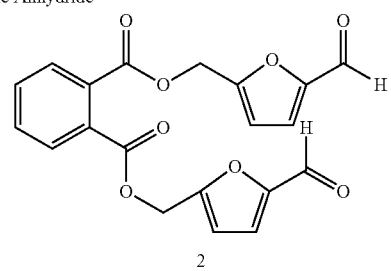

2

Charge HMF (5.00 g, 39.6 mmol) to the reactor under argon. Submerge the reactor into a preheated oil bath (130° C.). Add phthalic anhydride (2.94 g, 19.8 mmol) to the molten HMF with vigorous stirring and a high argon flow rate. Allow the HMF to solvate the phthalic anhydride. At this point, immediately add tetra-isopropyl titanate (Tyzor TPT®) (3.82×10⁻² mmol, 11.3 µL) to the reaction mixture. The mixture was allowed to stir under argon at 130° C. for 24 hours. The resultant product was a black viscous liquid containing approximately 30% di-ester and 21% mono-ester.

Example II-12

Di-ester was also prepared by treating mono-ester with a molar equivalent of carbonyldiimidazole (CDI) followed by HMF in acetonitrile. The solution was cooled to 0° C. and then stirred for 14 hours. Purification by column chromatography afforded pure di-ester in 40% yield.

Esterification reactions can be performed with PAN in combination with diols to form polyester derivatives that are typically useful for fibers, composites and the like. End capping is possible with HMF or HMF phthalic acid mono-esters or maleic acid mono-esters. Examples are shown below.

The unsaturated ester is typically used for homopolymerization or copolymerization with other unsaturated monomers, diols and polyols, such as polyester polyols derived from phthalic anhydride and diols such as diethylene glycol and 1,6-hexanediol.

Furandimethanol (FDM), HMF, and furan-2,5-dicarboxylic acid (FDCA) is typically used in the synthesis of polyester polyols by reactions with phthalic anhydride and diols such as diethylene glycol and 1,6-hexqanediol.

FDM, HMF and FDCA are typically used as capping agents and chain extenders for polyester polyols derived from phthalic anhydride and diols such as diethylene glycol (DEG), 1,6-hexanediol (HED) and furandimethanol (FDM).

Example Set III

Example III-1

Referring now to FIG. 1, this figure illustrates the reaction of FDM with diethylene glycol and/or another diol and PAN. Based on the reactions illustrated in the examples herein it is expected that the reactants shown in FIG. 1 can be driven to higher oligomers or polymers. The reaction proceeds at temperatures between 60° C. and 130° C. and with conditions and catalysts typical of those discussed above. Other useful diols may include 1,6-hexane diol, neopentyl glycol, cyclohexanedimethanol, other alkyl diols, polyethylene glycols, and polypropylene glycols. It is important to note that the product composition shown in FIG. 1 corresponds to a blocked copolymer system where statistical variation in paired components in the oligomer or polymer is expected. The value of n typically ranges from about 5 to about and the value of y typically ranges from about 5 to about 300. If desired, PAN may be replaced by phthalic acid isomers (e.g. isophthalic acid, terephthalic acid). Relative molar amounts of FDM, glycol and/or diol, and PAN are selected to obtain the desired composition.

Example III-2

Figure 2:
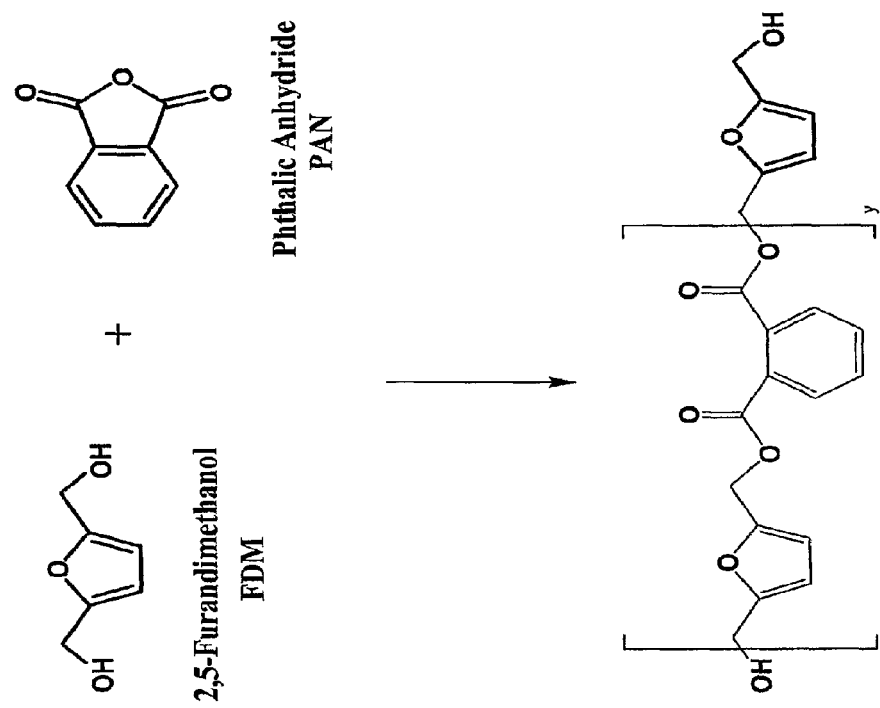
FIG. 2 illustrates the reaction of FDM with PAN

Referring now to FIG. 2, this figure illustrates the reaction of FDM with PAN. Based on the reactions illustrated in the examples herein it is expected that the reactants shown in FIG. 2 can be driven to higher oligomers or polymers. The reaction proceeds at temperatures between 60° C. and 130° C. and with conditions typical of those discussed above. It is important to note that the product composition shown in FIG. 2 corresponds to a blocked copolymer system where statistical variation in paired components in the oligomer or polymer is expected. The value of y typically ranges from about 5 to about 300. If desired PAN may be replaced by phthalic acid isomers (e.g. isophthalic acid, terephthalic acid).

Example III-3

Figure 3:
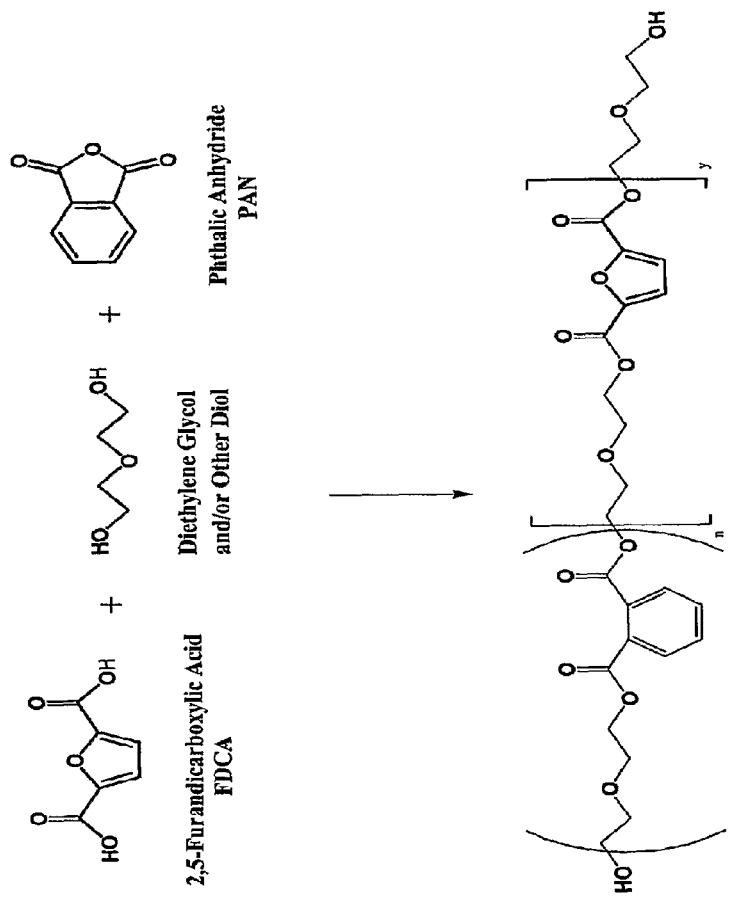
FIG. 3 illustrates the reaction of FDCA with diethylene glycol and/or another diol and PAN.

Referring now to FIG. 3, this figure illustrates the reaction of FDCA with diethylene glycol and/or another diol and PAN. Based on the reactions illustrated in the examples herein it is expected that the reactants shown in FIG. 3 can be driven to higher oligomers or polymers. The reaction proceeds at temperatures between 60° C. and 130° C. and with conditions and catalysts typical of those discussed above. Other useful diols may include 1,6-hexane diol, neopentyl glycol, cyclohexanedimethanol, other alkyl diols, polyethylene glycols, and polypropylene glycols. It is important to note that the product composition shown in FIG. 3 corresponds to a blocked copolymer system where statistical variation in paired components in the oligomer or polymer is expected. The value of n typically ranges from about 5 to about 300 and the value of y typically ranges from about 5 to about 300. If desired PAN may be replaced by phthalic acid isomers (e.g. isophthalic acid, terephthalic acid). Relative molar amounts of FDM, glycol and/or diol, and PAN are selected to obtain the desired composition.

Example III-4

Figure 4:
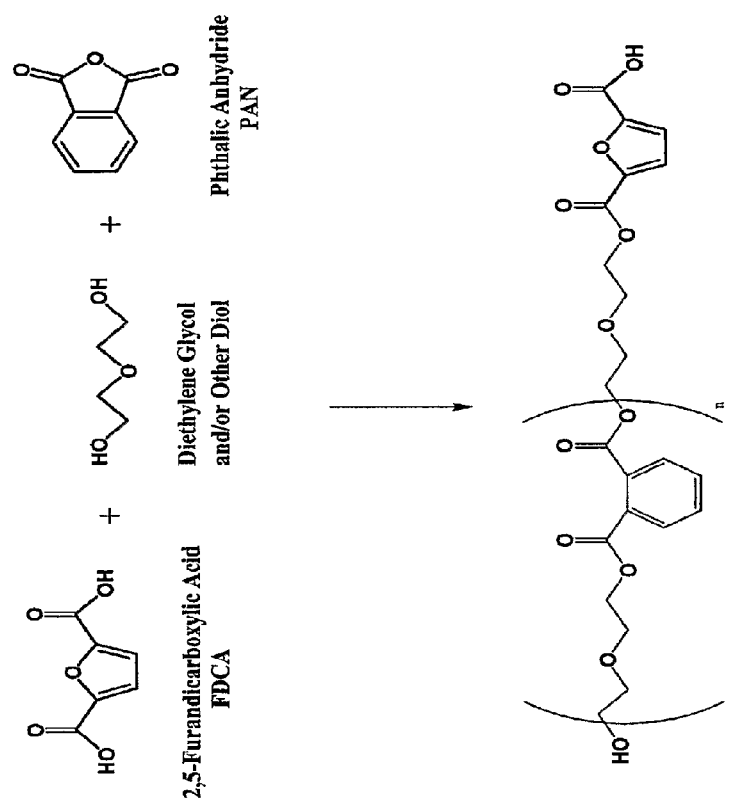
FIG. 4 illustrates the reaction of FDCA with diethylene glycol and/or another diol and PAN with lower molar amount of glycol or diol relative to PAN.

Referring now to FIG. 4, the procedure according to FIG. 3 above is repeated except that a lower molar amount of glycol or diol is used relative to PAN. This provides an oligomer or polymer where one end is terminated by a PAN derived moiety. The value of y typically ranges from about 5 to about 300. If desired PAN may be replaced by phthalic acid isomers (e.g. isophthalic acid, terephthalic acid).

Example III-5

Figure 5:
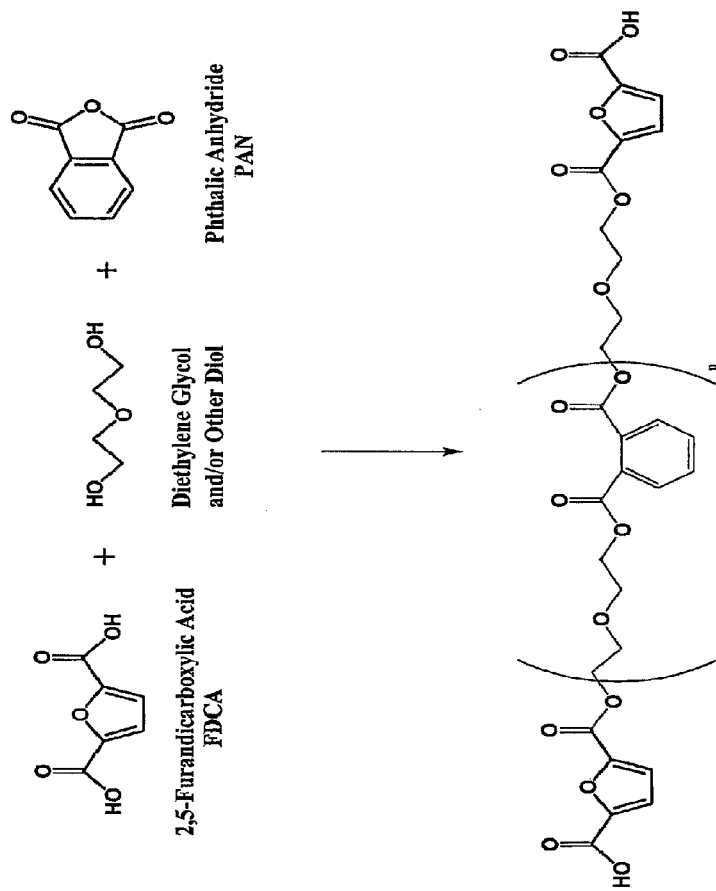
FIG. 5 illustrates the reaction of FDCA with diethylene glycol and/or another diol and PAN with lower molar amount of glycol or diol relative to PAN and FDCA.

Referring now to FIG. 5, the procedure according to FIG. 4 above is repeated except that a lower molar amount of glycol or diol is used relative to PAN and FDCA. This provides an oligomer or polymer where both ends are preferentially terminated by a PAN derived moiety. The value of n typically ranges from about 5 to about 300. If desired PAN may be replaced by phthalic acid isomers (e.g. isophthalic acid, terephthalic acid).

Example III-6

Figure 6:
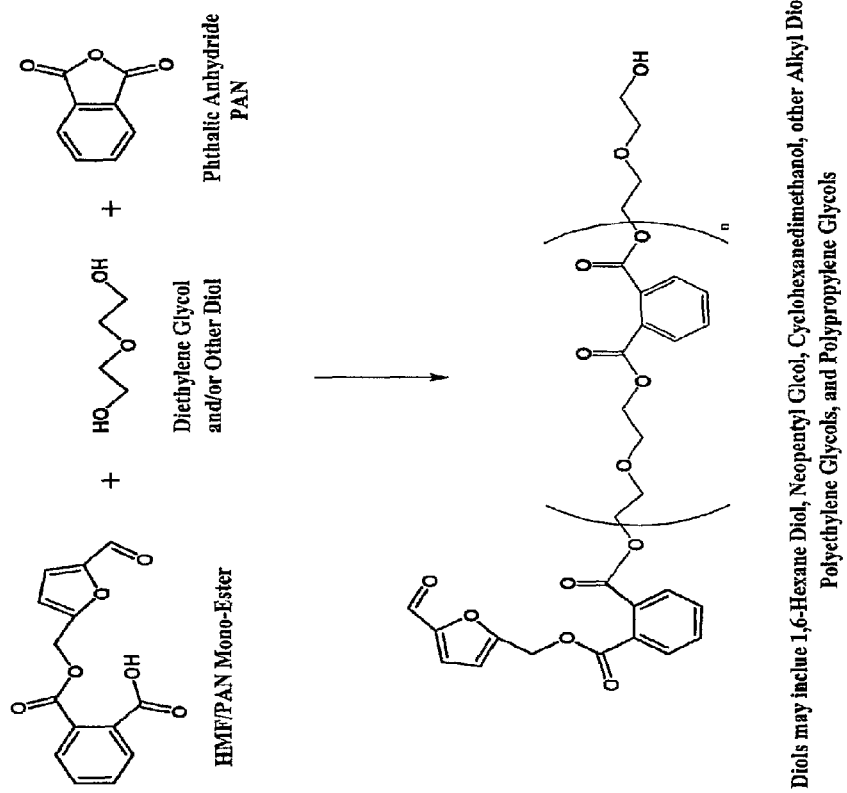
FIG. 6 illustrates the reaction of HMF/PAN mono-ester with diethylene glycol and/or another diol and PAN.

Referring now to FIG. 6, this figure illustrates the reaction of HMF/PAN mono-ester with diethylene glycol and/or another diol and PAN. Based on the reactions illustrated in the examples herein it is expected that the reactants shown in FIG. 6 can be driven to higher oligomers or polymers. The reaction proceeds at temperatures between 60° C. and 130° C. and with conditions and catalysts typical of those discussed above. Other useful diols may include 1,6-hexane diol, neopentyl glycol, cyclohexanedimethanol, other alkyl diols, polyethylene glycols, and polypropylene glycols. It is important to note that the product composition shown in FIG. 6 corresponds to a blocked copolymer system where statistical variation in paired components in the oligomer or polymer is expected. The value of n typically ranges from about 5 to about 300. If desired PAN may be replaced by phthalic acid isomers (e.g. isophthalic acid, terephthalic acid). Relative molar amounts of HMF/PAN mono-ester, glycol and/or diol, and PAN are selected to obtain the composition shown. The resulting product has single end capping with the mono-ester.

Example III-7

Figure 7:
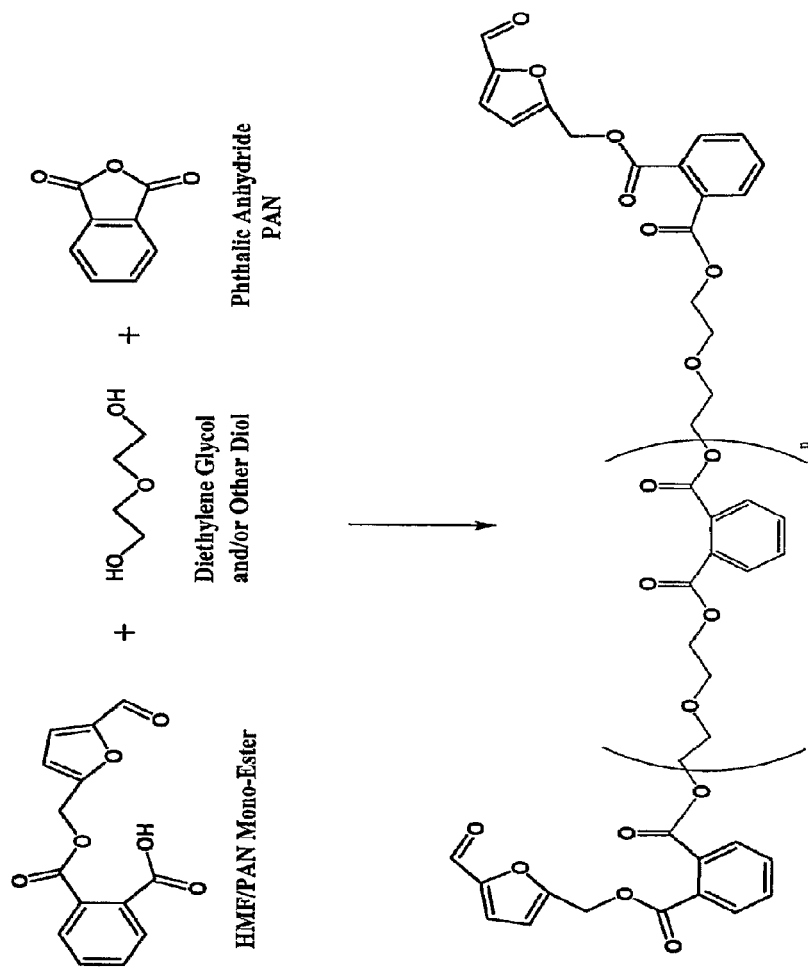
FIG. 7 illustrates the reaction of HMF/PAN mono-ester with diethylene glycol and/or another diol and PAN with a higher molar amount of HMF-PAN mono-ester.

Referring now to FIG. 7, the method according to FIG. 6 is repeated except that a higher molar amount of HMF-PAN mono-ester is used than in example 6. This results in double end capping with the mono-ester.

Example III-8

Figure 8:
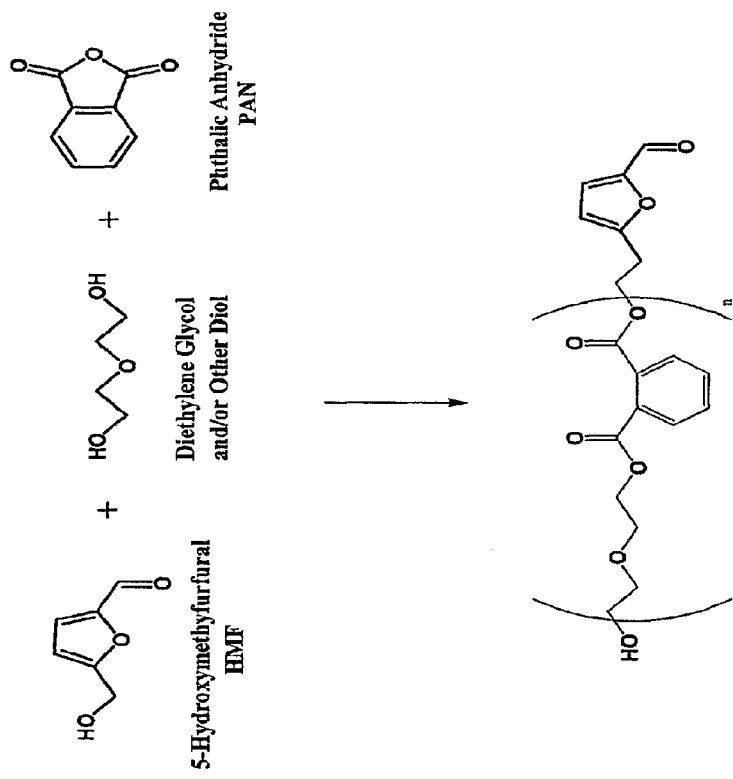
FIG. 8 illustrates the reaction of HMF with diethylene glycol and/or another diol and PAN.

Referring now to FIG. 8, this figure illustrates the reaction of HMF with diethylene glycol and/or another diol and PAN. Based on the reactions illustrated in the examples herein it is expected that the reactants shown in FIG. 8 can be driven to higher oligomers or polymers. The reaction proceeds at temperatures between 60° C. and 130° C. and with conditions and catalysts typical of those discussed above. Other useful diols may include 1,6-hexane diol, neopentyl glycol, cyclohexanedimethanol, other alkyl diols, polyethylene glycols, and polypropylene glycols. It is important to note that the product composition shown in FIG. 8 corresponds to a blocked copolymer system where statistical variation in paired components in the oligomer or polymer is expected. The value of n typically ranges from about 5 to about 300. If desired PAN may be replaced by phthalic acid isomers (e.g. isophthalic acid, terephthalic acid). Relative molar amounts of HMF, glycol and/or diol, and PAN are selected to obtain the composition shown. The resulting product has single end capping with HMF.

Example III-9

Figure 9:
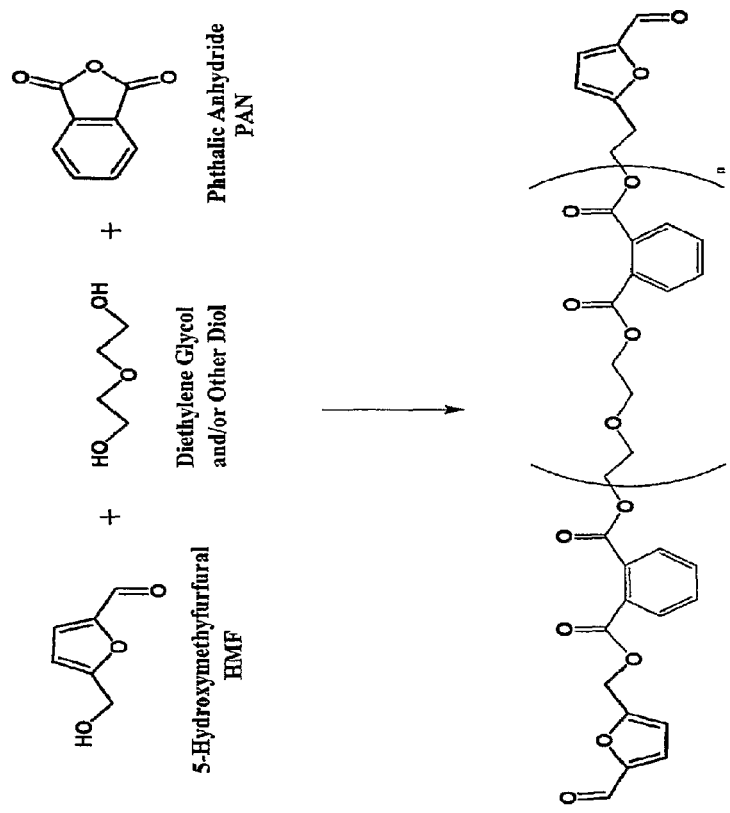
FIG. 9 illustrates the reaction of HMF with diethylene glycol and/or another diol and PAN with increased molar amounts of HMF.

Referring now to FIG. 9, the procedure according to FIG. 8 is repeated except that increased molar amounts of HMF favor and result in double end capping by HMF.

While the forms of the invention herein disclosed constitute presently preferred embodiments, many others are possible. It is not intended herein to mention all of the possible equivalent forms or ramifications of the invention. It is to be understood that the terms used herein are merely descriptive, rather than limiting, and that various changes may be made without departing from the spirit of the scope of the invention.

We claim:

1. A method for di-ester synthesis comprising:
   mixing 5-(hydroxymethyl)-2-furfuraldehyde and dimethyl phthalate with a suitable catalyst; and
   heating at about 80° C. to about 110° C. while stirring for about 2 to about 4 hours.

2. A method for di-ester synthesis comprising:
   melting 5-(hydroxymethyl)-2-furfuraldehyde:
   adding phthalic anhydride and an optional esterification catalyst to the molten 5-(hydroxymethyl)-2-furfuraldehyde while stirring; and
   reacting the mixture while stirring for about 16 to about 30 hours at a temperature between about 110° C. to about 140° C.

3. A method for di-ester synthesis comprising;
   mixing a mono-ester reaction product of 5-(hydroxymethyl)-2-furfuraldehyde and phthalic anhydride with a molar equivalent of a coupling reagent;
   adding 5-(hydroxymethyl)-2-furfuraldehyde to the mixture;
   cooling the mixture to between about −10° C. to about 10° C.; and
   reacting the cooled mixture for about 10 to 18 hours at the reduced temperature.

4. The method according to claim 3 wherein the coupling agent is CDI, BOP, PYBOP, or dicyclohexylcarbodiimide.

5. A method for producing a mono-ester and/or a di-ester comprising:
   a. contacting 5-(hydroxymethyl)-2-furfuraldehyde with a second reactant selected from maleic anhydride, maleic acid, fumaric acid, dimethylfumarate, phthalic anhydride, phthalic acid, phthalic acid diester, phthalic diacid chloride, isophthalic acid, isophthalic di-ester, isophthalic diacid chloride, terephthalic acid, terephthalic di-ester, terephthalic di-ester, or mixtures thereof in a reaction vessel; and
   b. reacting the contacting reactants to obtain the mono-ester and/or di-ester product.

6. The method according to claim 5, wherein the reaction involves a mole ratio of 5-(hydroxymethyl)-2-furfuraldehyde:maleic anhydride or 5-(hydroxymethyl)-2-furfuraldehyde:phthalic anhydride of 1:1 to 1:2 to obtain increased monoester product.

7. The method according to claim 6, wherein the reaction is at temperatures at which the reactants melt up to about 120° C.

8. The method according to claim 5, wherein 5-(hydroxymethyl)-2-furfuraldehyde and the second reactant are melted, wherein mono-ester product yield is increased versus di-ester product yield.

9. The method according to claim 5, wherein 5-(hydroxymethyl)-2-furfuraldehyde is added to either phthalic anhydride or maleic anhydride to obtain increased mono-ester product.

10. The method according to claim 5, wherein the mole ratio of 5-(hydroxymethyl)-2-furfuraldehyde:maleic anhydride is greater than about 2:1, wherein di-ester product yield is increased versus mono-ester product yield.

11. The method according to claim 7, wherein an optional catalyst and/or an optional water scavenger are used.

12. A method for producing an ester of 5-hydroxymethylfurfural comprising:
   a. mixing 5-(hydroxymethyl)-2-furfuraldehyde and phthalic anhydride; and
   b. reacting at a temperature between about 75° C. and about 150° C. to obtain the product.

13. The method according to claim 12, wherein the reaction is in the presence of a catalyst.

14. The method according to claim 12, wherein a mono-ester is obtained.

15. The method according to claim 12, wherein a di-ester is obtained.

16. The method according to claim 12, wherein a mixture of a mono-ester and a di-ester is obtained.

17. The method according to claim 12, further comprising:
   c. separating the product from the reactant mixture.

18. The method according to claim 12, wherein the reaction is carried out in the presence of an inert gas to exclude air from the reaction.

19. The method according to claim 13 wherein the catalyst is selected from pyridine; (dimethylamino)pyridine; organic titanates; dibutyltin dilaurate; dibutyltin oxide; tin(II) chloride; magnesium ethoxide; carbodiimides; molecular sieves; basic or acidic ion exchange resins; toluene-sulfonic acid; sulfuric acid; HCl; aluminum chloride; boron trifluoride; boron trifluoride diethyletherate; clay; lanthanide complexes; or cation radicals.

20. A method for producing a di-ester comprising:
   reacting 5-(hydroxymethyl)-2-furfuraldehyde and dimethyl phthalate at an elevated temperature in the presence of a catalyst,
   wherein the ratio of 5-(hydroxymethyl)-2-furfuraldehyde: dimethyl phthalate is about 2:1 to about 5:1.

21. The method according to claim 20, wherein the temperature is above about 60° C.

* * * * *